US006458390B1

(12) United States Patent
Manelski et al.

(10) Patent No.: US 6,458,390 B1
(45) Date of Patent: Oct. 1, 2002

(54) LONG WEARING MAKEUP COMPOSITIONS

(75) Inventors: Jean Marie Manelski, Spring Lake, NJ (US); Neil D. Scancarella, Wyckoff, NJ (US); Julio Gans Russ, Westfield, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 09/916,362

(22) Filed: Jul. 27, 2001

(51) Int. Cl.$^7$ .................. A01N 59/16; A61K 33/24; A61K 33/26
(52) U.S. Cl. ........................ 424/617; 424/646
(58) Field of Search .................... 424/63, 646, 617

(56) References Cited

U.S. PATENT DOCUMENTS

| | | | |
|---|---|---|---|
| 4,828,826 A | 5/1989 | Franz | 424/63 |
| 5,324,506 A | 6/1994 | Calvo | 424/63 |
| 5,460,804 A | 10/1995 | Krzysik | 424/60 |
| 5,480,632 A | 1/1996 | Orr | 424/63 |
| 5,512,272 A | 4/1996 | Krzysik | 424/59 |
| 5,599,547 A | 2/1997 | Bartholomey | 424/401 |
| 5,609,852 A | 3/1997 | Galley | 424/59 |
| 5,609,854 A * | 3/1997 | Guerrero et al. | 424/59 |
| 5,622,694 A | 4/1997 | Torgerson | 424/70.122 |
| 5,849,275 A | 12/1998 | Calello | 424/64 |
| 5,851,517 A | 12/1998 | Mougin | 424/78.02 |
| 5,874,072 A | 2/1999 | Alwattari | 424/70.7 |
| 5,916,547 A | 6/1999 | Torgerson | 424/70.12 |
| 5,919,547 A | 7/1999 | Torgerson | 424/70.122 |
| 5,932,197 A | 8/1999 | Arnaud | 424/64 |
| 5,945,095 A | 8/1999 | Mougin | 424/78.02 |
| 5,985,258 A | 11/1999 | Alwattari | 424/70.7 |
| 6,180,123 B1 | 1/2000 | Mondet | 424/401 |
| 6,024,946 A | 2/2000 | Dubief | 424/70.1 |
| 6,083,516 A | 7/2000 | Curtis | 424/401 |
| 6,126,929 A | 10/2000 | Mougin | 424/70.7 |
| 6,139,823 A | 10/2000 | Drechsler | 424/64 |
| 6,159,486 A | 12/2000 | Terren | 424/401 |
| 6,214,329 B1 | 4/2001 | Brieva | 424/70.7 |

FOREIGN PATENT DOCUMENTS

| | | | |
|---|---|---|---|
| EP | 497144 | * | 1/1992 |
| EP | 1084696 | * | 3/2001 |
| JP | 08239223 | * | 9/1996 |

OTHER PUBLICATIONS

Phoenix Chemical, Inc., Giovarez AC–5099M, Jan. 1, 1999.

* cited by examiner

*Primary Examiner*—Alton Pryor
(74) *Attorney, Agent, or Firm*—Julie Blackburn

(57) ABSTRACT

A single phase gel based makeup composition containing one or more iron oxide pigments, a film forming silicone acrylate copolymer solvated in volatile solvent, and one or more non-wax gelling agents capable of gelling the composition to a viscosity of at least about 1,000 centipoise at room temperature, and the use of such compositions either alone or emulsified into a polar phase.

20 Claims, No Drawings

LONG WEARING MAKEUP COMPOSITIONS

TECHNICAL FIELD

The invention is in the field of compositions for application to eyebrows and eyelashes to impart color, or for use in lining the eyes with color, or application to the skin as in a facial or body tattoo, or the lips as a semi-permanent lipcolor.

BACKGROUND OF THE INVENTION

Many women use a variety of products to beautify the eyes, including brow color, eye shadow, mascara, and eyeliner. Such products accentuate the eyes and in the case of lash products, will also give the appearance of longer lashes.

One of the common problems with eye products such as liners and mascara is that they often do not wear for long periods of time and have a tendency to smudge. With respect to eyeliner, more adventurous consumers have addressed this problem by having "permanent" eyeliner essentially tattooed onto the eyelids. This is a permanent cosmetic procedure and the eyeliner is not removable.

Cosmetic manufacturers are constantly exploring new formulas for such products that will fill the need gaps of longer wear and reduced smudging in a way that will not necessitate visits to beauty salons to have permanent cosmetics tattooed into the skin. The desired cosmetics should provide long lasting, durable wear, preferably one or more days, and be removable by the consumer whenever desired. In addition, the color should be rich and as natural looking as possible.

Typically, products for making up the eyes contain inorganic iron oxide pigments in an emulsion. Iron oxides are water insoluble and are generally ground with one or more oils in the composition to form what is referred to as a pigment grind. For example, traditional mascaras are mixtures of waxes, oils, and inorganic pigments. They may be anhydrous or in the emulsion form. Many of the so-called water resistant mascaras are anhydrous or contain minimal amounts of water, while traditional mascaras are often in the emulsion form. These types of mascaras are generally applied to the lashes and wear for periods of time ranging from several hours to one day. Users usually remove what remains of such products at the end of the day by washing with water. Another problem associated with such mascaras is their tendency to smudge when the user becomes warm or wears eye makeup that is oily. Moreover, since such products contain significant levels of wax and oil, the inorganic pigments that provide color may tend to be muted. This in turn provides a more artificial look to mascara coated lashes.

Similarly, eyeliner is usually a liquid product or in a pencil form. It is applied to the upper and lower lids to accentuate the eye area. While eyeliner is a very desirable beauty product, it tends to smudge very readily, especially when worn on lower lashes. The smudging is due, in part to the solubilizing of the dried eyeliner formula by skin oils, perspiration, and tears. Again, the iron oxides typically used to provide color to such products are muted and matte in tone, sometimes providing an artificial look to the liner especially when the color is very dark.

The major need gaps in the field of lash, brow, lip, and liner products relates to creating a color that has a rich, deep, natural tone, and at the same time providing a product that has the capability of extended wear (one or more days) if desired by the consumer, and where negative tendencies such as smudging upon exposure to perspiration, tears, and environmental assaults are reduced or eliminated. Because inorganic pigments are inexpensive and widely available, it is desirable to use inorganic pigments in such compositions.

The object of the invention is to prepare products for making up the eyes and skin, such as mascara compositions (or lash tints), brow color, eyeliner, lip color, facial or body tattoos that exhibit extended wear, look natural, provide a rich color, and exhibit reduced smudging.

Another object of the invention is to provide eye products that are capable of wearing for one to five days and provide a natural appearance.

Another object of the invention is to provide commercially acceptable, stable, products for making up the eyes.

SUMMARY OF THE INVENTION

The invention is directed to a single phase gel based makeup composition containing one or more iron oxide pigments, a film forming silicone acrylate copolymer solvated in volatile solvent, and one or more non-wax gelling agents capable of gelling the composition to a viscosity of at least about 1,000 centipoise at room temperature.

The invention is further directed to a single phase gel based makeup composition containing one or more iron oxide pigments, a film forming silicone acrylate copolymer solvated in volatile solvent, and one or more non-wax gelling agents capable of gelling the composition to a viscosity of at least about 1,000 centipoise at room temperature, wherein the composition is substantially free of waxes which are animal and vegetable derived lipids.

The invention is directed to a single phase gel based makeup composition containing one or more iron oxide pigments, a film forming silicone acrylate copolymer solvated in volatile solvent, and one or more non-wax gelling agents capable of gelling the composition to a viscosity of at least about 1,000 centipoise at room temperature wherein said composition is substantially free of non-ionic emulsifiers.

The invention is further directed to a single phase gel based makeup composition containing one or more iron oxide pigments, a film forming silicone acrylate copolymer solvated in volatile solvent, and one or more non-wax gelling agents capable of gelling the composition to a viscosity of at least about 1,000 centipoise at room temperature, wherein the composition is substantially free of (a) waxes which are animal and vegetable derived lipids and (b) nonionic emulsifiers.

The invention is also directed to a method for preparing an emulsion makeup composition comprising preparing a single phase gel composition containing one or more iron oxide pigments, a film forming silicone acrylate copolymer solvated in volated solvent, and one or more non-wax gelling agents wherein the single phase gel portion of the emulsion has a viscosity of at least about 1,000 centipoise at room temperature and combining said single phase gel composition with a polar phase to form an emulsion.

DETAILED DESCRIPTION

I. Single Phase Gel Composition

The claimed composition is gel based, which means that it is in a viscous gel-like form, e.g. semi-solid or viscous liquid. Preferably the composition has a viscosity ranging from about 1000 to 500,000, more preferably 5000 to 250,000, most preferably 7000 to 120,000 centipoise at room temperature (room temperature being bout 25° C.).

The composition may be used as eyeliner, eyecolor, lashcolor, lipcolor, or a tattoo, or in any other fashion where extended wear is desirable. The compositions general exhibit wear that is longer than one day, and up to three days.

The composition exists in a single phase. The term "single phase" means that the composition exists in one homogeneous phase which contains the inorganic pigments, the film forming silicone acrylate copolymer solvated in volatile solvent, and the non-wax gelling agent. The term "solvated" means that the silicone acrylate copolymer may be dissolved or solubilized in the volatile solvent either in whole or in part, or dispersed in the volatile solvent. In both cases the silicone acrylate copolymer must be compatible with the volatile solvent. Similarly, the pigments may be solvated in the single phase composition, which means they are either solubilized or dispersed therein, and are compatible and stable therein. In either case, when the composition is applied to the desired surface, the volatile solvent evaporates at least in part and the film forming polymer sets on the surface trapping the pigment particles that were dispersed or solubilized in that phase on the surface. The ingredients found in this composition are further described herein.

Preferably the claimed compositions are substantially anhydrous. The term "substantially" means that the claimed compositions contain less than about 5%, preferably less than about 2%, preferably less than about 1%, water. The most preferred compositions of the invention are anhydrous.

A. Iron Oxide Pigments

The claimed composition contains 0.001–25%, preferably about 0.005–10%, more preferably about 0.1–8% by weight of the total composition of one or more inorganic pigments. Suitable pigments include iron oxides such as red, blue, black, green, and yellow; titanium dioxide, bismuth oxychloride, and the like. The iron oxides may be surface treated if desired, with hydrophobic agents such as silicone, lecithin, mineral oil, or similar materials. The surface treatment will cause the pigment to be generally hydrophobic in nature and favor the lipophilic phase of the composition.

B. Film Forming Silicone Acrylate Copolymer

The claimed compositions comprise one or more silicone acrylate copolymers that are capable of forming a film when incorporated into the claimed composition and applied to the desired surface. The composition preferably comprises 0.1–85, preferably 0.1–35%, more preferably 1–25% by weight of the total composition of one or more silicone acrylate film forming polymers. The film forming polymer (or film former) may be soluble or dispersible in the volatile solvent and when the composition is applied to the desired surface, the solvent at least partially evaporates and causes the film forming polymer to form a film on the surface which holds the pigment particles in place with the network created by the hardened polymer. The term "soluble" means that the film forming polymer is soluble in the volatile solvent and when combined both components form a homogeneous single phase. The term "dispersible" means that the film forming polymer is readily dispersed in the volatile solvent and forms a stable, heterogeneous composition where the dispersed polymer remains stable in the volatile solvent and is not incompatible therewith. The film forming polymer also has adhesive properties, meaning that when incorporated into the claimed composition and applied to the lashes, the film forming polymer forms a film or a weld on the lashes. Such a film will have adhesive and cohesive strength, as is understood by those skilled in the art. Further, the preferred film forming polymer will be capable of forming an semi-permanent film on the surface to which it is applied, meaning that the composition containing the polymer is not removed from the surface to which it is applied with simple soap and water after application and once it has adequately dried and set.

Suitable silicone acrylate copolymers are in general copolymers of silicone and ethylenically unsaturated monomers. The resulting copolymers may be graft or block copolymers. The term "graft copolymer" is familiar to one of ordinary skill in polymer science and is used herein to describe the copolymers which result by adding or "grafting" polymeric side chain moieties (i.e. "grafts") onto another polymeric moiety referred to as the "backbone". The backbone may have a higher molecular weight than the grafts. Thus, graft copolymers can be described as polymers having pendant polymeric side chains, and which are formed from the "grafting" or incorporation of polymeric side chains onto or into a polymer backbone. The polymer backbone can be a homopolymer or a copolymer. The graft copolymers are derived from a variety of monomer units. One type of silicone acrylate copolymer that may be used as the film forming polymer is a vinyl-silicone graft or block copolymer having the formula:

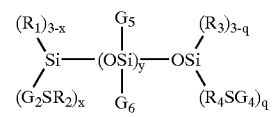

wherein $G_5$ represents monovalent moieties which can independently be the same or different selected from the group consisting of alkyl, aryl, aralkyl, alkoxy, alkylamino, fluoroalkyl, hydrogen, and —ZSA; A represents a vinyl polymeric segment consisting essentially of a polymerized free radically polymerizable monomer, and Z is a divalent linking group such as $C_{1-10}$ alkylene, aralkylene, arylene, and alkoxylalkylene, most preferably Z methylene or propylene.

$G_6$ is a monovalent moiety which can independently be the same or different selected from the group consisting of alkyl, ayl, aralkyl, alkoxy, alkylamino, fluoroalkyl, hydrogen, and —ZSA;

$G_2$ comprises A;

$G_4$ comprises A;

$R_1$ is a monovalent moiety which can independently be the same or different and is selected from the group consisting of alkyl, aryl, aralkyl, alkoxy, alkylamino, fluoroalkyl, hydrogen, and hydroxyl; but preferably $C_{1-4}$ alkyl or hydroxyl, and most preferably methyl.

$R_2$ is independently the same or different and is a divalent linking group such as $C_{1-10}$ alkylene, arylene, aralkylene, and alkoxyalkylene, preferably $C_{1-3}$ alkylene or $C_{7-10}$ aralkylene, and most preferably —CH$_2$— or 1,3-propylene, and $R_3$ is a monovalent moiety which is independently alkyl, aryl, aralkyl, alkoxy, alkylamino, fluoroalkyl, hydrogen, or hydroxyl, preferably $C_{1-4}$ alkyl or hydroxyl, most preferably methyl;

$R_4$ is independently the same or different and is a divalent linking group such as $C_{1-10}$ alkylene, arylene, aralkylene, alkoxyalkylene, but preferably $C_{1-3}$ alkylene and $C_{7-10}$ alkarylene, most preferably —CH$_2$— or 1,3-propylene.

x is an integer of 0–3;

y is an integer of 5 or greater; preferably 10 to 270, and more preferably 40–270; and q is an integer of 0–3.

These polymers are described in U.S. Pat. No. 5,468,477, which is hereby incorporated by reference. Most preferred is poly(dimethylsiloxane)-g-poly(isobutyl methacrylate), which is manufactured by 3-M Company under the tradename 3M Silicone Plus Polymer VS 70. This polymer may be purchased in the dry particulate form, or as a solution where the polymer is dissolved in one or more volatile solvents such as isododecane. Preferred is where the polymer is in dry particulate form, and as such it can be dissolved in one or more of the volatile solvents found in the gel composition. This polymer has the CTFA name Polysilicone-6.

Another type of such a polymer comprises a vinyl, methacrylic, or acrylic backbone with pendant siloxane groups and pendant fluorochemical groups. Such polymers preferably comprise comprise repeating A, C, D and optionally B monomers wherein:

A is at least one free radically polymerizable acrylic or methacrylic ester of a 1, 1,-dihydroperfluoroalkanol or analog thereof, omega-hydridofluoroalkanols, fluoroalkylsulfonamido alcohols, cyclic fluoroalkyl alcohols, and fluoroether alcohols, B is at least one reinforcing monomer copolymerizable with A, C is a monomer having the general formula X(Y)nSi(R) 3–m Z.m wherein
X is a vinyl group copolymerizable with the A and B monomers,
Y is a divalent linking group which is alkylene, arylene, alkarylene, and aralkylene of 1 to 30 carbon atoms which may incorporate ester, amide, urethane, or urea groups,
n is zero or 1;
m is an integer of from 1 to 3,
R is hydrogen, $C_{1-4}$ alkyl, aryl, or alkoxy,
Z is a monovalent siloxane polymeric moiety; and D is at least one free radically polymerizable acrylate or methacrylate copolymer.

Such polymers and their manufacture are disclosed in U.S. Pat. Nos. 5,209,924 and 4,972,037, which are hereby incorporated by reference. More specifically, the preferred polymer is a combination of A, C, and D monomers wherein A is a polymerizable acrylic or methacrylic ester of a fluoroalkylsulfonamido alcohol, and where D is a methacrylic acid ester of a $C_{1-2}$ straight or branched chain alcohol, and C is as defined above. An example is a polymer having the general formula:

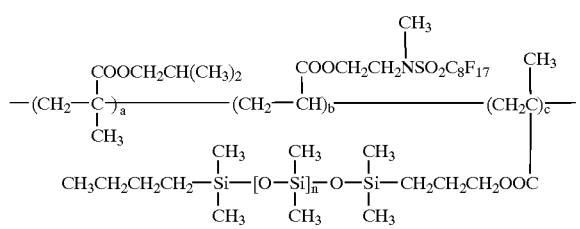

wherein each of a, b, and c has a value in the range of 1–100,000, and the terminal groups are selected from the group consisting of a $C_{1-20}$ straight or branched chain alkyl, aryl, and alkoxy and the like. These polymers may be purchased from Minnesota Mining and Manufacturing Company under the tradenames "Silicone Plus" polymers. Most preferred is poly(isobutyl methacrylate-co-methyl FOSEA)-g-poly(dimethylsiloxane) which is sold under the tradename SA 70-5 IBMMF.

Another suitable silicone acrylate copolymer is a polymer having a vinyl, methacrylic, or acrylic polymeric backbone with pendant siloxane groups. Such polymers as disclosed in U.S. Pat. Nos. 4,693,935, 4,981,903, 4,981,902, and which are hereby incorporated by reference. Preferably, these polymers are comprised of A, C, and optionally B monomers wherein:

A is at least on free radically polymerizable vinyl, methacrylate, or acrylate monomer;

B, when present, is at least one reinforcing monomer copolymerizable with A,

C is a monomer having the general formula:

$$X(Y)_nSi(R)_{3-m}Z_m$$

wherein:
X is a vinyl group copolymerizable with the A and B monomers;
Y is a divalent linking group;
n is zero or 1;
m is an integer of from 1 to 3;
R is hydrogen, $C_{1-10}$ alkyl, substituted or unsubstituted phenyl, $C_{1-10}$ alkoxy; and
Z is a monovalent siloxane polymeric moiety.

Examples of A monomers are lower to intermediate methacrylic acid esters of $C_{1-12}$ straight or branched chain alcohols, styrene, vinyl esters, vinyl chloride, vinylidene chloride, acryloyl monomers, and so on.

The B monomer, if present, is a polar acrylic or methacrylic monomer having at least one hydroxyl, amino, or ionic group (such as quaternary ammonium, carboxylate salt, sulfonic acid salt, and so on).

The C monomer is as above defined.

Most preferred is where the film forming polymer comprises Polysilicone-6, which is a dry particulate material that may be used as is or solubilized in one or more ingredients that form the volatile solvent.

Examples of other suitable copolymers that may be used herein, and their method of manufacture, are described in detail in U.S. Pat. No. 4,693,935, Mazurek, U.S. Pat. No. 4,728,571, and Clemens et al., both of which are incorporated herein by reference. Additional grafted polymers are also disclosed in EPO Application 90307528.1, published as EPO Application 0 408 311, U.S. Pat. No. 5,061,481, Suzuki et al., U.S. Pat. No. 5,106,609, Bolich et al., U.S. Pat. No. 5,100,658, Bolich et al., U.S. Pat. No. 5,100,657, Ansher-Jackson, et al., U.S. Pat. No. 5,104,646, Bolich et al., U.S. Pat. No. 5,618,524, issued Apr. 8, 1997, all of which are incorporated by reference herein in their entirety.

C. Volatile Solvent

The claimed compositions comprise one or more volatile solvents for solvating the silicone acrylate film forming polymer. Suggested ranges of volatile solvent range from about 0.1–85%, preferably 0.5–80%, more preferably 10–75% by weight of the total composition. The term "volatile" means that the oil has a measurable vapor pressure, or a vapor pressure of at least 2 mm of mercury at 20° C. Suitable volatile solvents are liquids and enable easy formulation of the composition of the invention. When the composition of the invention is applied to the desired surface, the volatile solvent of the invention must be capable of flashing off to leave the other ingredients in the composition affixed to the surface. Suitable volatile solvents generally have a viscosity of 0.5 to 10 centipoise at 25° C. Suitable volatile solvents include linear silicones, cyclic silicones, paraffinic hydrocarbons, or mixtures thereof.

1. Volatile Silicones

Cyclic silicones (or cyclomethicones) are of the general formula:

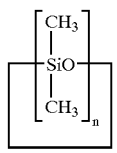

where n=3–6.

Linear volatile silicones in accordance with the invention have the general formula:

$$(CH_3)_3Si\text{—}O\text{—}[Si(CH_3)_2\text{—}O]_n\text{—}Si(CH_3)_3$$

where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

2. Paraffinic Hydrocarbons

Also suitable as the volatile liquid are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable.

Particularly preferred as the volatile solvent is isododecane either alone or in combination with a volatile silicone. More preferred is where the ratio of volatile solvent to silicone acrylate copolymer 1:1 to 10:1 respectively. Most preferred are compositions containing greater than about 45 to 50% by weight of the total composition of volatile solvent.

D. Non-wax Gelling Agent

The claimed composition is gelled with one or more non-wax gelling agents. The term "non-wax" means that the gelling agent is not a relatively high melting point (e.g. 35 to 170° C.) animal or vegetable derived lipid. Suggested ranges of non-wax gelling agents are about 0.01–60%, preferably about 0.05–50%, more preferably about 0.1–45% by weight of the total composition. Suitable non-wax gelling agents include natural or synthetic montmorillonite minerals such as hectorite, bentonite, and quaternized derivatives thereof which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like. Particularly preferred is Quaternium-18 hectorite.

Also suitable as the non-wax gelling agents are various polymeric compounds known in the art as associative thickeners. Suitable associative thickeners generally contain a hydrophilic backbone and hydrophobic side groups. Examples of such thickeners include polyacrylates with hydrophobic side groups, cellulose ethers with hydrophobic side groups, polyurethane thickeners. Examples of hydrophobic side groups are long chain alkyl groups such as dodecyl, hexadecyl, or octadecyl; alkylaryl groups such as octylphenyl or nonyphenyl Another type of non-wax gelling agent that may be used in the compositions are silicas, silicates, silica silylate, and derivatives thereof These silicas and silicates are generally found in the particulate form. Particularly preferred is silica.

Other types of non-wax gelling agents that may be used fit into the category of particulate fillers and include ingredients such as titanated mica, polymethylmethacrylate, micronized teflon, boron nitride, acrylate copolymers, aluminum starch octenylsuccinate, calcium silicate, cellulose, chalk, corn starch, diatomaceous earth, fuller's earth, kaolin, maltodextrin, microcrystalline cellulose, rice starch, silk powder, talc, mica, zinc laurate, zinc myristate, zinc rosinate, alumina, calcium carbonate, dextran, nylon, sericite, soy flour, tin oxide, titanium hydroxide, trimagnesium phosphate, walnut shell powder, or mixtures thereof The above mentioned particulates may be surface treated with lecithin, amino acids, mineral oil, silicone oil or various other agents either alone or in combination, which coat the powder surface and render the particles more lipophilic in nature.

E. Other Ingredients

1. Plasticizers

It is desirable to incorporate one more plasticizers into the composition. Since the preferred compositions may have a lower viscosity when compared to standard mascaras, the plasticizer will improve the spreadability and application of the composition to the surface to which it is applied. The preferred compositions contain one or more plasticizers in an amount sufficient to improve spreadability and application of the composition when compared to the same composition without the plasticizer. Suggested ranges of plasticizers range from about 0.01–20%, preferably about 0.05–15%, more preferably about 0.1–10% by weight of the total composition. A variety of plasticizers are suitable including Suitable plasticizers include glyceryl, glycol, and citrate esters as disclosed in U.S. Pat. No. 5,066,484, which is hereby incorporated by reference. Examples of such esters include glyceryl tribenzoate, glyceryl triacetate, acetyl tributyl citrate, dipropylene glycol dibenzoate, and the like. Also suitable, are plasticizers of the following general formula:

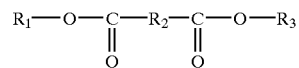

wherein $R_1$, $R_2$, and $R_3$ are each independently a $C_{1-20}$ straight or branched chain alkyl or alkylene which may be substituted with one or more hydroxyl groups. Preferably, $R_1$ is a $C_{3-10}$ straight or branched chain alkyl; $R_2$ is a $C_{2-8}$ alkyl which may be substituted with one or more hydroxyl groups; and $R_3$ is a $C_{3-10}$ straight or branched chain alkyl. Examples of such compounds include dioctyl malate, diisopropyl adipate, dibutyl adipate, dibutyl sebacate, dioctyl azelate, dioctyl succinate, dioctyl fumarate, and the like. Preferred is where $R_1$ and $R_3$ are a branched $C_8$ alkyl, $R_2$ is a $C_2$ alkyl substituted with one hydroxy group, which is dioctyl malate.

Preferred plasticizers are the glycerol, glycol and citrate esters, in particular acetyl tributyl citrate and dibutyl adipate.

2. Non-volatile Oils

The preferred compositions comprise one or more non-volatile liquid oils such as silicones, organic esters, and the like. If present, ranges of about 0.01–45%, preferably about 0.1–40%, more preferably about 0.5–35% by weight of the total composition are suitable. The term "non-volatile" means that the oil has a vapor pressure of less than 2 mm. of mercury at 20° C. The non-volatile oils should not be too heavy or greasy as it may hamper the long wearing characteristics of the invention. Generally, the viscosity of the nonvolatile oils if present should range from about 11–1000, preferably less than 100 centipoise, most preferably less than about 50 centipoise at 25° C. Examples of such oils include polyalkylsiloxanes, polyarylsiloxanes, and polyethersiloxanes. Examples of such nonvolatile silicones are disclosed in Cosmetics, Science and Technology 27–104 (Balsam and Sagarin ed. 1972); and U.S. Pat. Nos. 4,202,879 and 5,069,897, both of which are hereby incorporated by references. Further nonlimiting examples of such silicones include dimethicone, phenyl trimethicone, dimethicone copolyol, and so on.

Also suitable are lower viscosity organic liquids including saturated or unsaturated, substituted or unsubstituted branched or linear or cyclic organic compounds that are liquid under ambient conditions. Preferred organic liquids include those described in U.S. Pat. Nos. 5,505,937; 5,725,845; 5,019,375; and 6,214,329, all of which are incorporated by reference herein in their entirety.

In the preferred compositions, the nonvolatile oil is present at less than about 5% by weight of the total composition, more preferably less than about 2.5% by weight. The most preferred compositions may not contain any non-volatile oil at all.

3. Preservatives

The claimed composition may comprise one or more preservatives such as methyl, ethyl, or propyl paraben, and so on, in amounts ranging from about 0.0001–5% by weight of the total composition.

G. Wax Free

In the most preferred embodiment of the invention, the claimed composition is gelled with one or more non-wax gelling agents and is substantially free of waxes which are animal or vegetable derived lipids, more particularly animal and vegetable derived lipids, preferably those having a melting point of 45 to 170° C., for example, waxes such as castor wax, ceresin, rice wax. The term "substantially free" means that the composition contains less than 5%, preferably less than 2% more preferably less than 1%, most preferably no waxes that are animal or vegetable derived lipids. The limited use of waxes is desirable because in traditional mascaras waxes tend to promote undesirable effects such as smudging. The use of certain low melting point or liquid waxes may be desirable in the claimed composition, including those set forth in U.S. Pat. Nos. 5,725,845, and 5,505,937 which are hereby incorporated by reference.

H. Emulsifier Free

In another most preferred embodiment of the invention the claimed composition is substantially free of non-ionic emulsifiers. Without being bound by this explanation, it is believed that the substantial absence of non-ionic emulsifiers in the formula contributes to the extended wear properties of the claimed composition because of the affinity of the hydrophilic portion of the emulsifier for water. In particular, without being bound by this explanation, when emulsifiers are present in the claimed composition which is then applied to the desired surface, when the wearer is exposed to water such as in swimming or showering, the hydrophilic portion of the emulsifier found in the cosmetic film has affinity for the water and tends to bind water molecules. That in turn contributes to easier removal of the composition from the skin or hair. The term substantially free means that the claimed compositions contain less than 5%, preferably less than 2% more preferably contain 0% of non-ionic emulsifiers, preferably non-ionic emulsifiers having HLB values ranging from about 4 to 8, and include compounds such as alkoxylated alcohols or ethers formed by the reaction of an alcohol with an alkylene oxide, usually ethylene or propylene oxide. Examples of such emulsifiers include Beheneth 5–30, which is formed by the reaction of behenyl alcohl and ethylene oxide where the number of repeating ethylene oxide units is 5 to 30, ceteareth-2–100 formed by the reaction of a mixture of cetyl and stearyl alcohols and ethylene oxide wherein the number of repeating ethylene oxide units is 2 to 100, Ceteth 1–45 which is formed by the reaction of cetyl alcohol and ethylene oxide, and the number of repeating ethylene oxide units is 1 to 45, Oleth 1–100 which is formed by the reaction of oleyl alcohol and ethylene oxide, and so on. If desired the alkoxylated alcohol may be reacted with one or more salts such as sodium, potassium, phosphate, and the like.

The claimed composition is also preferably substantially free of alkoxylated carboxylic acids formed by the reaction of a carboxylic acid with an alkylene oxide or with a polymeric ether. The resulting products have the general formula:

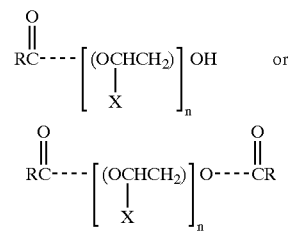

where RCO is the carboxylic ester radical, X is hydrogen or lower alkyl, and n is the number of polymerized alkoxy groups. In the case of the diesters, the two RCO—groups do not need to be identical. Preferably, R is a $C_{6-30}$ straight or branched chain, saturated or unsaturated alkyl, and n is from 1–100.

The claimed compositions are also preferably free of nonionic surfactants which are monomeric, homopolymeric and block copolymeric ethers. Such ethers are formed by the polymerization of monomeric alkylene oxides, generally ethylene or propylene oxide. Such polymeric ethers have the following general formula:

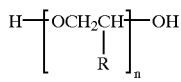

wherein R is H or lower alkyl and n is the number of repeating monomer units, and ranges from 1 to 500.

The claimed compositions are also preferably substantially free of other nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

In the most preferred embodiment of the invention the claimed compositions are substantially free of animal or vegetable derived lipid waxes and non-ionic emulsifiers.

The claimed compositions may be used as described, or they may be emulsified into water or other polar ingredients to form an emulsion of the gel based composition in one or more polar ingredients such as water, alcohols, etc.

The invention will be further described in connection with the following examples which are set forth for the purposes of illustration only.

EXAMPLE 1

A composition suitable for use as a mascara, eyeliner, browcolor, tattoo was made as follows:

|  | w/w % |
|---|---|
| Isododecane | 29.15 |
| Dimethicone (1 centipoise) | 20.00 |
| Polysilicone 6 | 20.35 |
| Quaternium-18 hectorite/isododecane/propylene carbonate (10:89:1) | 18.00 |
| Silica | 6.00 |
| Black iron oxide | 3.50 |
| Dibutyl adipate | 2.40 |
| Methyl paraben | 0.30 |
| Propyl paraben | 0.30 |

The polysilicone 6 was dissolved in isododecane and dimethicone. This mixture was combined with the remaining ingredients and mixed well.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A single phase gel based makeup composition containing one or more iron oxide pigments, a film forming silicone acrylate copolymer solvated in volatile solvent, having a vapor pressure of at least 2 mm mercury at 20° C. and one or more non-wax gelling agents capable of gelling the composition to a viscosity of at least about 1,000 centipoise at room temperature.

2. The composition of claim 1 wherein the silicone acrylate copolymer comprises polydimethylsiloxane-g-polyC$_{1-12}$ alkyl methacrylate.

3. The composition of claim 2 wherein the silicone acrylate copolymer comprises polydimethylsiloxane-g-polyisobutylmethacrylate.

4. The composition of claim 1 wherein the volatile solvent comprises a paraffinic hydrocarbon, a linear silicone, a cyclic silicone, or mixtures thereof.

5. The composition of claim 4 wherein the volatile solvent comprises a mixture of a paraffinic hydrocarbon having 5 to 20 carbon atoms and a linear silicone.

6. The composition of claim 5 wherein the volatile paraffinic hydrocarbon is isododecane.

7. The composition of claim 4 wherein the linear silicone comprises dimethicone having a viscosity of 0.5–10 centipoise at room temperature.

8. The composition of claim 1 comprising, by weight of the total composition:

10–85% volatile solvent,

1–35% silicone acrylate copolymer, 0.1–45% non-wax gelling agent, and 0.1–25% iron oxide pigments.

9. The composition of claim 8 wherein the volatile solvent comprises a mixture of paraffinic hydrocarbon and linear or cyclic silicones.

10. The composition of claim 9 wherein the paraffinic hydrocarbon is isododecane.

11. The composition of claim 9 wherein the linear silicone is dimethicone having a viscosity of 0.5 to 10 centipoise at room temperature.

12. The composition of claim 9 wherein the ratio of paraffinic hydrocarbon to silicone acrylate copolymer is about 1:1 to 10:1.

13. The composition of claim 1 which contains more than about 45% by weight of the total composition of volatile solvent.

14. The composition of claim 1 which contains less than about 5% by weight of non-volatile oil.

15. A single phase gel based makeup composition containing one or more iron oxide pigments, a film forming silicone acrylate copolymer solvated in volatile solvent, having a vapor pressure of at least 2 mm mercury at 20° C. and one or more non-wax gelling agents capable of gelling the composition to a viscosity of at least about 1,000 centipoise at room temperature wherein said composition is substantially free of waxes which are animal or vegetable derived lipids.

16. The composition of claim 15 which is free of waxes which are animal and vegetable derived lipids having a melting point of 45 to 170° C.

17. A single phase gel based makeup composition containing one or more iron oxide pigments, a film forming silicone acrylate copolymer solvated in volatile solvent, having a vapor pressure of at least 2 mm mercury at 20° C. and one or more non-wax gelling agents capable of gelling the composition to a viscosity of at least about 1,000 centipoise at room temperature wherein said composition is substantially free of non-ionic emulsifiers.

18. A single phase gel based makeup composition containing one or more iron oxide pigments, a film forming silicone acrylate copolymer solvated in volatile solvent, having a vapor pressure of at least 2 mm mercury at 20° C. and one or more non-wax gelling agents capable of gelling the composition to a viscosity of at least about 1,000 centipoise at room temperature wherein said composition is substantially free of both (a) waxes which are animal or vegetable derived lipids, and (b) non-ionic emulsifiers.

19. The composition of claim 18 which is a mascara, browcolor, tattoo, or eyeliner.

20. A method for preparing an emulsion makeup composition comprising preparing a single phase gel composition containing one or more iron oxide pigments, a film forming silicone acrylate copolymer solvated in volatile solvent, having a vapor pressure of at least 2 mm mercury at 20° C. and one or more non-wax gelling agents wherein the single phase gel portion of the emulsion has a viscosity of at least about 1,000 centipoise at room temperature and combining said single phase gel composition with a polar phase to form an emulsion.

* * * * *